(12) United States Patent
Schaefer et al.

(10) Patent No.: US 9,388,803 B2
(45) Date of Patent: Jul. 12, 2016

(54) TUBE ROLLER PUMP INCLUDING A PIVOTABLE TUBE SUPPORT AND MEDICAL DEVICE FOR EXTRACORPOREAL BLOOD TREATMENT

(71) Applicant: B. BRAUN AVITUM AG, Melsungen (DE)

(72) Inventors: Oliver Schaefer, Neuenstein (DE); Andreas Iske, Melsungen (DE); Bjoern Broeker, Staufenberg (DE)

(73) Assignee: B. Braun Avitum AG, Melsungen (DE)

( * ) Notice: Subject to any disclaimer, the term of this patent is extended or adjusted under 35 U.S.C. 154(b) by 310 days.

(21) Appl. No.: 13/933,624

(22) Filed: Jul. 2, 2013

(65) Prior Publication Data

US 2014/0010690 A1    Jan. 9, 2014

(30) Foreign Application Priority Data

Jul. 3, 2012 (DE) .......................... 10 2012 105 926

(51) Int. Cl.
*F04B 43/08* (2006.01)
*F04B 43/12* (2006.01)
(Continued)

(52) U.S. Cl.
CPC ............. *F04B 43/08* (2013.01); *F04B 43/1261* (2013.01); *F04B 43/1284* (2013.01); *F04B 53/22* (2013.01); *A61M 1/14* (2013.01)

(58) Field of Classification Search
CPC .... F04B 43/08; F04B 43/0072; F04B 43/123; F04B 43/12; F04B 43/1238; F04B 43/1261; F04B 43/1284; F04B 43/1292; F04B 53/22; F04B 53/1253; F04B 45/08; F04B 39/14; A61M 1/14
USPC ........ 417/477.3, 477.7, 477.8, 477.9, 477.11, 417/477.12, 474, 476
See application file for complete search history.

(56) References Cited

U.S. PATENT DOCUMENTS 3,011,684 A * 12/1961 Corneil .......................... 222/214
3,963,023 A * 6/1976 Hankinson ...................... 604/19
(Continued)

FOREIGN PATENT DOCUMENTS

DE    38 72 053    11/1988
EP    1 241 355    9/2002
(Continued)

OTHER PUBLICATIONS

13933624—Espacenet Translation of JP2008000425A Jan. 10, 2008.*
(Continued)

*Primary Examiner* — Devon Kramer
*Assistant Examiner* — Jon Hoffmann
(74) *Attorney, Agent, or Firm* — RatnerPrestia (57) ABSTRACT

Medical devices for extracorporeal blood treatment including tube roller pumps. Tube roller pumps including a pump housing having a bent bearing surface and a rotor being rotatable inside the bearing surface, wherein a tubing segment can be introduced between the bearing surface and the rotor in the form of a loop. A stationary first receiving portion for accommodating one end of the loop-shaped tubing segment and a rocker arm including a second receiving portion for accommodating the other end of the loop-shaped tubing segment is located at the pump housing, wherein the rocker arm is rotatable about a pivoting axis so that the second receiving portion with the tubing segment can be brought into at least two different positions and that a first position represents a threading position and a second position represents an unthreading position for the tubing segment.

15 Claims, 7 Drawing Sheets

(51) Int. Cl.
*F04B 53/22* (2006.01)
*A61M 1/14* (2006.01)

(56) References Cited

U.S. PATENT DOCUMENTS

| | | | | |
|---|---|---|---|---|
| 4,363,609 | A * | 12/1982 | Cosentino | F04B 43/1276 417/477.5 |
| 4,798,580 | A | 1/1989 | DeMeo et al. | |
| 7,037,092 | B2 * | 5/2006 | Kagawa et al. | 417/476 |
| 7,134,374 | B1 * | 11/2006 | Williamson | E21B 29/04 166/54.5 |
| 7,223,079 | B2 * | 5/2007 | Ortega | F04B 43/1253 417/477.3 |
| 7,722,338 | B2 * | 5/2010 | Nordell | F04B 43/1253 417/477.11 |
| 7,980,835 | B2 * | 7/2011 | LaBanco | F04B 43/12 417/477.12 |
| 8,047,819 | B2 * | 11/2011 | Lawrence et al. | 417/477.1 |
| 8,052,399 | B2 * | 11/2011 | Stemple | F04B 43/1284 417/476 |
| 2005/0095152 | A1 * | 5/2005 | Dale | A61L 2/0088 417/477.2 |
| 2008/0213113 | A1 * | 9/2008 | Lawrence | A61M 1/1037 417/476 |
| 2009/0129944 | A1 * | 5/2009 | Stemple et al. | 417/53 |
| 2009/0234289 | A1 * | 9/2009 | Gagel | F04B 43/1253 604/151 |
| 2011/0300010 | A1 * | 12/2011 | Jarnagin | A61B 17/3207 417/477.2 |
| 2012/0082576 | A1 | 4/2012 | Beck et al. | |
| 2014/0012176 | A1 * | 1/2014 | Schaefer | A61M 1/3621 604/6.16 |

FOREIGN PATENT DOCUMENTS

| | | |
|---|---|---|
| JP | 7 059 845 | 3/1995 |
| JP | 2008 000 425 | 1/2008 |
| JP | 2008000425 A * | 1/2008 |

OTHER PUBLICATIONS

13933624—Espacenet translation of JP200800425A.*
German Search Report for DE 10 2012 105 926.8 Issued Jan. 17, 2013.
European Search Report for EP 13174673.7 dated Oct. 14, 2013.

* cited by examiner

TUBE ROLLER PUMP INCLUDING A PIVOTABLE TUBE SUPPORT AND MEDICAL DEVICE FOR EXTRACORPOREAL BLOOD TREATMENT

CROSS REFERENCE TO RELATED APPLICATIONS

This application claims priority to German Patent Application No. DE 10 2012 105 926.8, filed Jul. 3, 2012, the contents of such application being incorporated by reference herein.

FIELD OF THE INVENTION

The invention relates to a tube roller pump for a medical device for extracorporeal blood treatment comprising a pump housing having a bent bearing surface and a rotor rotatable inside the bearing surface, a tubing segment being adapted to be introduced between the bearing surface and the rotor in loop shape.

The invention further relates to a medical device for extracorporeal blood treatment comprising such tube roller pump.

BACKGROUND INFORMATION

In medical devices for extracorporeal blood treatment (dialysis) frequently tube roller pumps are used for feeding the collected blood of the patient to a dialyser and back to the patient. Said tube roller pumps function as peristaltic pumps, wherein a loop-shaped tubing segment is adjacent to an appropriately bent bearing surface of the pump housing. A rotor of the pump located inside the bearing surface then moves with its outer edges along the tubing segment, wherein it locally impresses the tube and thus enables feeding of blood through the tubing segment by the elastic material properties of the tubing segment. For this purpose, the blood is fed to the tubing segment via a first port and is discharged again via another port at the other end of the tubing segment.

The tubing segment thus forms a transfer system, as it is called, e.g. together with the feeding and discharging lines and several air traps, by which transfer system the blood of the patient is fed to a dialyser and back to the patient. Those transfer systems are preferably exchanged after each treatment and are not re-used for other patients. A used tubing segment thus has to be removed from the pump before a new transfer system is introduced into the device. For facilitating the handling during removal and rigging of the transfer system it is further known to provide a connector adapted to be connected to a feeding and discharging line, respectively, at each of the two ends of the tubing segment.

For accommodating a tube inside a roller pump the U.S. Pat. No. 8,047,819 B2, for example, describes holding means that are detachably mounted on the pump housing. So for different sizes and types of tubes different holding means can be mounted on the pump. A holding means includes a clamping device including at least one pivoting clamp jaw having a semicircular recess so that a tube can be held in said semicircular recess and an opposed equally semicircular recess of another clamp jaw. The clamp jaws can also include plural of said recesses so that plural tubes can be simultaneously accommodated.

Moreover automatic systems are known that are intended to take over and thus facilitate threading and unthreading of the tube into the pump. Frequently, for unthreading an actuator moving the system from its therapy position into an unthreading position via a linear drive, for instance, has to be operated. For this purpose, it can be required in those systems to operate a switch/button at the medical device or to touch a software button on user interface.

Furthermore, multi-connectors are known which combine both terminals for feeding and discharging lines in one component part which then can be introduced into a receiving portion of the pump housing. Via the geometric shape of such multi-connectors it is possible to detect the presence thereof in the pump by the fact that during the inserting operation for instance a cylindrical portion of the multi-connector operates a plunger the axial position of which is queried via a light barrier. At the same time this plunger is part of an electromechanical actuator mounted in the pump housing which is adapted to eject the multi-connector via a linear drive.

In order to move a tubing segment at a tube roller pump into the respective threading and unthreading position, e.g. from JP 2008-000425 several variants of a pivoting member or rocker arm are known to which both ends of the loop-shaped tubing segment can be fastened. In a first pivoting position of the rocker arm the tubing segment then is provided in a position in which the threading operation can be started while the tubing segment can be unthreaded in a different pivoting position. The automatic threading and unthreading operation is performed by guide pins at the periphery of the rotor, the guide pins pressing the tube into the pump housing or out of the latter upon rotation of the rotor.

Both ends of the loop-shaped tubing segment are lifted and lowered, respectively, by the rocker arm so that the guide pins have to be appropriately shaped so as to be capable of catching the tube in said two positions and pressing it into a particular direction. The automatic threading and unthreading operation must be adapted to be reliably implemented, but the tube must not be deformed too strongly.

SUMMARY OF THE INVENTION

Based on this, it is the object of the invention to provide a tube roller pump for a medical device for extracorporeal blood treatment which enables a tubing segment to be arranged so that the tubing segment can be threaded into and unthreaded from the tube roller pump in an automated manner.

It is another object of the invention to provide a medical device for extracorporeal blood treatment comprising such tube roller pump.

The tube roller pump according to aspects of the invention is suited for a medical device for extracorporeal blood treatment and includes a pump housing having a bent bearing surface and a rotor rotatable inside the bearing surface, wherein a tubing segment can be introduced between the bearing surface and the rotor in loop shape. According to aspects of the invention, at the pump housing a stationary first receiving portion for accommodating one end of the loop-shaped tubing segment and a rocker arm including a second receiving portion for accommodating the other end of the loop-shaped tubing segment are provided, the rocker arm being rotatable about a pivoting axis so that the second receiving portion with the tubing segment can be brought into at least two different positions and that a first position constitutes a threading position and a second position constitutes an unthreading position for the tubing segment.

This configuration of the tube roller pump helps to arrange a tubing segment on a pump housing in a simple manner. One end of a loop-shaped tubing segment can be introduced into a receiving portion at the pump housing, the receiving portion being stationary and the tubing segment thus being fixed at the pump housing in this area. The other end of the loop-shaped tubing segment, on the other hand, is introduced into the receiving portion at the rocker arm so that the tubing segment is movable in this area. Thus this area of the tubing segment can be brought both into a threading position and into an unthreading position.

Preferably the receiving portions are in the form of undercut recesses into which the elastic tubing segment can be pressed. In the wake of the therapy the tube can be removed from the receiving portions again.

Furthermore means for automated threading and unthreading of the tubing segment between the rotor and the bearing surface can be provided at the rotor. For instance at the periphery of the rotor at least one guide pin is disposed which upon rotation of the rotor contacts the tube and forces the same into a specific direction. The second receiving portion is then provided in the unthreading position at a position at which the at least one guide pin moves between the tubing segment and the bottom of the pump housing upon rotation of the rotor and thus can lift the tubing segment out of the pump housing. By pivoting the rocker arm away from the pump housing the second receiving portion and thus the tubing segment is lifted so far that the at least one guide pin can unthread the tubing segment.

In contrast to this, the second receiving portion is provided in the threading position at a position at which the at least one guide pin moves above the tubing segment upon rotation of the rotor and hereby the tubing segment can be pressed into the pump housing. By pivoting the rocker arm the tubing segment is thus moved above or below the at least one guide pin so that the latter is adapted to carry out the threading or unthreading operation.

It is a particular advantage of the stationary first receiving portion that this receiving portion is not lifted or lowered but is fixed to the pump housing so that in this area no pinching of the tube will take place. In this way the risk of hemolysis during the therapy is reduced so that especially during the threading operation before the therapy it is important for the tube not to be badly deformed. Therefore the stationary first receiving portion preferably is the receiving portion in the direction of which the tube is slightly pushed by the at least one guide pin during threading.

In an embodiment of the invention means for maintaining the rocker arm in the threading position are provided at the tube roller pump. For this, for example aside the pivoting axis means for locking the rocker arm with the pump housing can be provided so that the rocker arm and thus the second receiving portion with the tubing segment can be manually pivoted into the threading position by an operator and are maintained there by themselves. For this purpose, at the pump housing a stop catch forming a stop mechanism together with the geometry of the rocker arm can be formed, wherein the locking takes place in the area of the second receiving portion.

Moreover, preferably also means for maintaining the rocker arm in the unthreading position are provided. They, too, can be realized in the form of a stop mechanism, wherein a stop catch forming a stop mechanism at the rocker arm together with a stop spring is configured at the pump housing. This stop spring can be bent and can be arranged in the area of the pivoting axis at the rocker arm, the bending of the stop spring extending substantially around the pivoting axis.

In order to be able to detect the respective position of the rocker arm at the different position the geometry and/or the material of the rocker arm can be configured so that the rocker arm can be detected at least in the threading position and in the unthreading position directly by detecting means at the tube roller pump. As soon as these positions have been clearly detected, the automated threading and/or unthreading operation can be initiated.

Different detecting mechanisms can be applied. For example, at the rocker arm at least one magnet and/or a ferromagnetic material is/are arranged. The plastic material of which the rocker arm is made can be injected around the magnet, for example, or the magnet is plasticized. A magnetically acting sensor system e.g. including Hall sensors at various positions then enables different positions of the rocker arm to be detected. In this embodiment of the invention, the detection is thus effected at least via the material properties of the rocker arm, because a magnetic area has to be provided; but also the geometry of the component part is crucial in order to be able to safely detect the various positions of the rocker arm. For this purpose, the magnet has to be arranged in a defined area, wherein such area may be specifically formed so as to detect the same by the sensor system.

This applies mutatis mutandis to an embodiment of a rocker arm in which at least a ferromagnetic material is arranged at the base member and/or the connector elements. The ferromagnetic material, too, can be surrounded by injection of plastic material, for example. It is possible in this way to detect different positions of the rocker arm by an inductively acting sensor system, with the detection being performed by way of the geometry and the material properties.

The different positions can also be detected. In another embodiment of the invention the rocker arm is opaque or light dispersive in at least one area, for example, and a transparent breakout is provided adjacent to the area or within the area. The rocker arm can be transparent outside the opaque or light dispersive area or the entire rocker arm is designed to be an opaque or light dispersive area. In this embodiment of the invention, the rocker arm position is detected via the geometry and the material properties of the rocker arm, these properties being used for an optical detection.

In such configuration of a rocker arm it is possible, for example, to determine by at least one light barrier in which position the rocker arm is just provided, for the light of a light barrier is either interrupted, when it is incident on an opaque or light dispersive area, or can penetrate the base member in the area of the breakout. An at least partly transparent rocker arm has the advantage that light cannot only be guided through the same in order to be detected by a light barrier. Rather, the position of the transmitting diodes of the light barrier can also be selected more freely, for there is the possibility that the light of a light barrier first penetrates a transparent partial area of the rocker arm, before it impinges on a breakout or an opaque or light dispersive area. This facilitates the configuration of the sensor system at the pump housing.

In another embodiment of the rocker arm the geometry and the material of the rocker arm form a light conductor through which the light is conductive along a defined path through the rocker arm. The light conductor preferably is configured so that light is conductive from the pivoting axis through the rocker arm to the second receiving portion. By appropriately arranging at least one transmitting diode that couples light into the rocker arm and at least one receiving diode that receives light out of the rocker arm different positions of the rocker arm can be detected by means of a sensor system by appropriately arranging the diodes in the different positions.

Furthermore, the invention includes a medical device for extracorporeal blood treatment comprising at least a tube roller pump including a pump housing having a bent bearing surface and a rotor rotating inside the bearing surface, wherein a tubing segment of an extracorporeal blood circulation can be introduced between the bearing surface and the rotor and blood can be fed to the tubing segment via a feeding line, while blood can be discharged from the tubing segment via a discharging line. In accordance with the invention, the device comprises a tube roller pump according to one of the described embodiments.

BRIEF DESCRIPTION OF THE DRAWINGS

The invention is best understood from the following detailed description when read in connection with the accompanying drawings. Included in the drawings are the following figures.

DETAILED DESCRIPTION OF EMBODIMENTS

Figure 1:
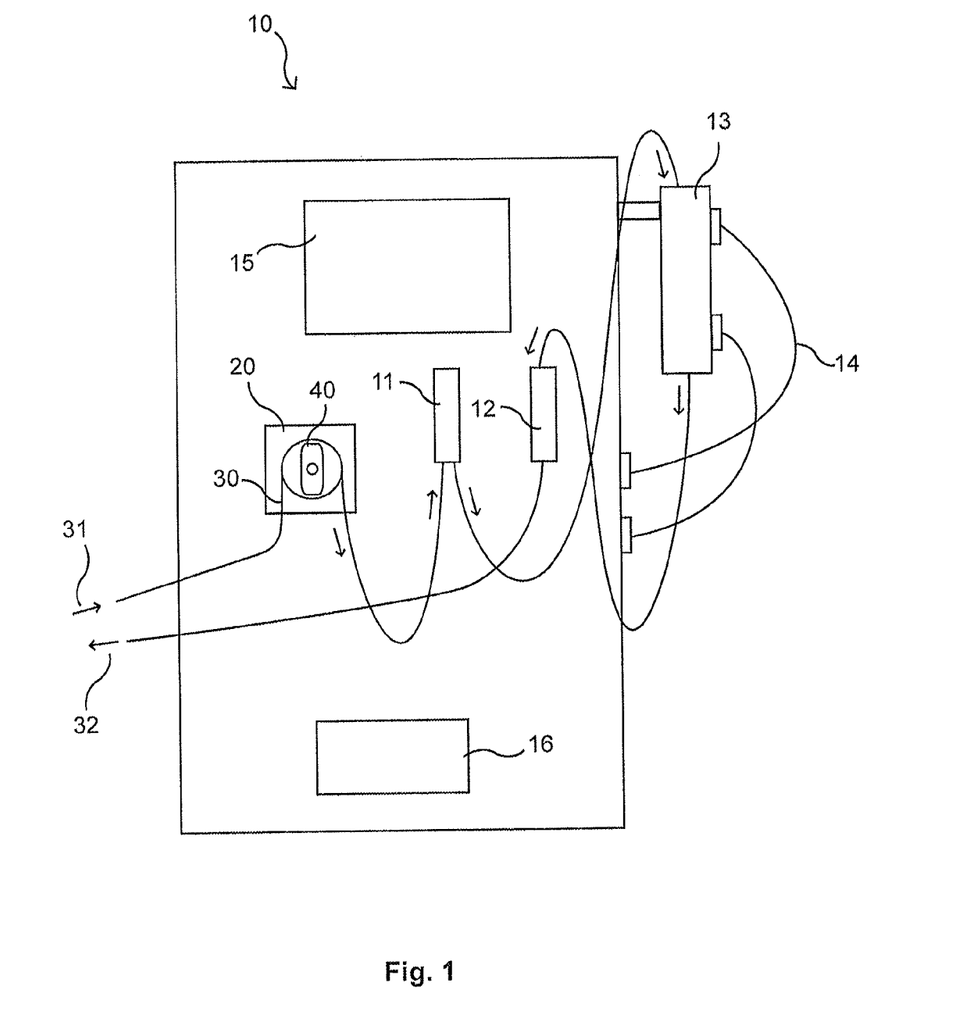
FIG. 1 a schematic representation of a medical device for extracorporeal blood treatment with a blood pump.

FIG. 1 shows a schematic representation of the substantial basic components of a medical device 10 for extracorporeal blood treatment with a blood pump, wherein the blood pump is a tube roller pump. The tube roller pump includes a pump housing 20 typically disposed at the front side of the dialyser 10.

Arterial blood 31 of a patient is fed to said tube roller pump and conveyed through the extracorporeal blood circulation. Subsequently the blood is returned to the patient as venous blood 32. The blood is delivered via the pump through a transfer system connected to plural components of the dialyser 10, a tubing segment 30 of the transfer system being inserted in the blood pump and a rotor 40 delivering the blood through this tubing segment 30 in a peristaltic manner, as it can be inferred from an enlarged view of FIG. 2.

After passing the blood pump the blood arrives at the dialyser 13 after it has preferably passed an arterial air trap 11 before. In the dialyser 13 the blood is purified by exchange of substance with a dialysate 14 which is fed to and discharged from the dialyser 13. After passing the dialyser 13 the blood arrives at a venous air trap 12 and is subsequently fed to the patient. This circulation of the patient's blood is marked by arrows in FIG. 1.

Parameters of the dialysis can be adjusted and the therapy can be monitored via a display/input unit 15 preferably in the form of a touchscreen. Furthermore the dialyser 13 includes a control unit 16.

Figure 2:
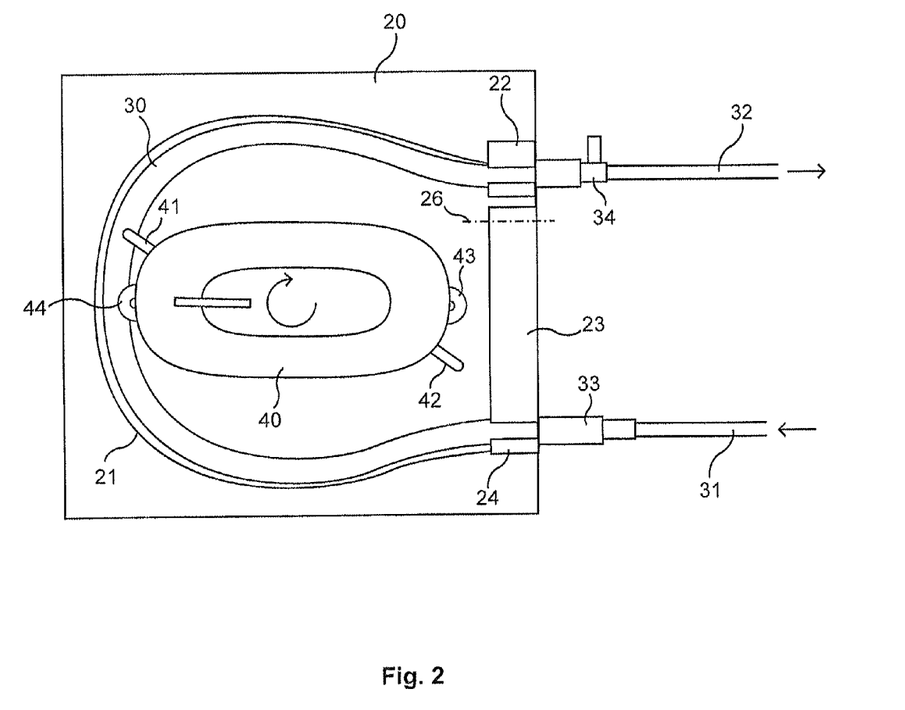
FIG. 2 a schematic top view on a tube roller pump including an inserted tubing segment.

FIG. 2 represents a schematic view of a tube roller pump including an inserted tubing segment 30. The tube roller pump includes the pump housing 20 which is easily accessible for the operator of the device, wherein it can be covered by a cover 50 (not shown in FIG. 2) which is pivotable for example upward or sideward via a hinge so as to get access to the pump.

By an indentation in the housing a curved bearing surface 21 is formed in the pump housing 20 into which bearing surface the tubing segment 30 can be inserted in loop shape so that its two tube ends are protruding from the housing 20. The indentation can be formed to having a side face in the pump housing 20 which extends substantially evenly normal to the front side of the device, or the bearing surface 21 is shaped unevenly by a side face of the indentation which is concave or even twisted in itself.

Inside the bearing surface 21 a rotor 40 having an elliptical circumference is arranged so that it can punctually compress the tubing segment 30 at its vertices during rotation. At said vertices or other areas pressing rollers 43 and 44 are arranged for this purpose. By clockwise rotation of the rotor 40 the area of a compressed tubing segment 30 moves equally clockwise until the corresponding vertex or the pressing roller 44 detaches from the tubing segment 30 again. In this period of time the opposed vertex or the pressing roller 43 has already contacted the tubing segment 30 again, however, so that blood is delivered in the respective area of the tubing segment 30 ahead of which it is compressed by the rotor 40 from the pump inlet to the pump outlet in a peristaltic manner. The rotor can also take any other suited shape apart from an elliptical circumference, however.

The tubing segment 30 is connected to a feeding line 31 and a discharging line 32 via connecting elements 33 and 34, as it is the case with standard transfer systems. One end of the tubing segment 30 is introduced in a first receiving portion 22 formed in the upper area of the pump housing 20. Said receiving portion 22 is fixedly integrated in the pump housing 20 and is formed as undercut recess so that the tubing segment 30 is pressed into this longitudinal slit. However, it can also be in the form of a longitudinally slotted sleeve tightly connected to the pump housing 20.

Below the upper receiving portion 22 a rocker arm 23 rotatable about a pivoting axis 26 is articulated. At the pivotable end of the rocker arm 23 a second receiving portion 24 is formed which is likewise an undercut recess into which the other end of the tubing segment 30 can be pressed. The connecting elements 33 and 34 for connecting the feeding and discharging lines 31, 32 are outwardly adjacent to the receiving portions 22 and 24 with the respective end of the tubing segment 30 so that the feeding and discharging lines 31, 32 cannot be pulled into the pump.

Figure 3:
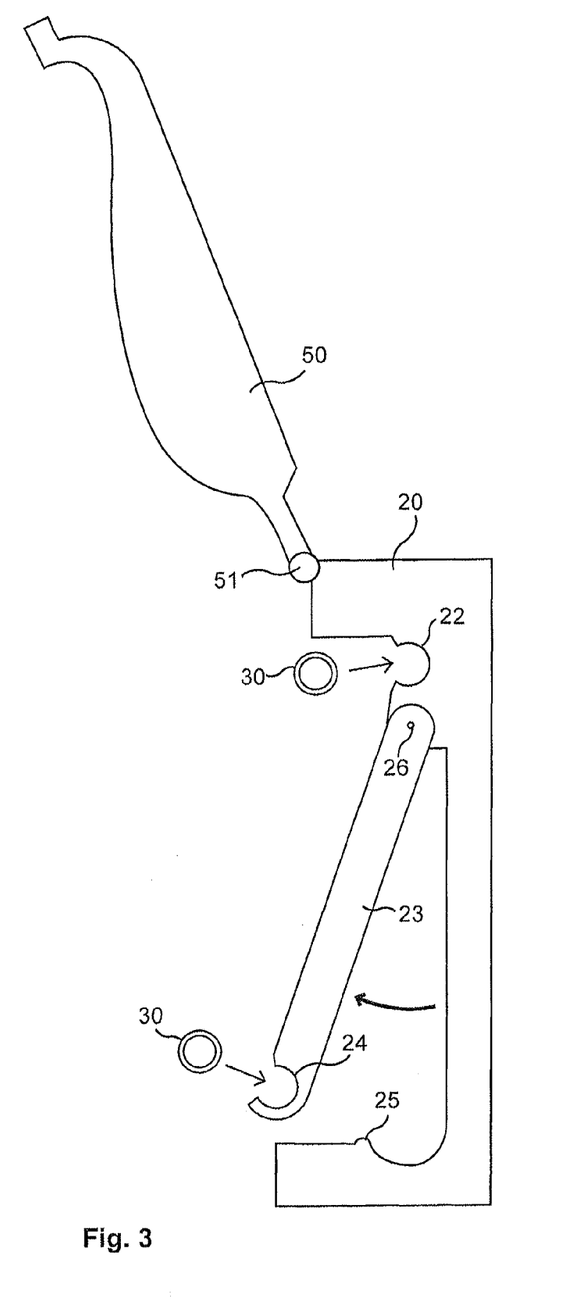
FIG. 3 a schematic side view of a tube roller pump according to FIG. 2 upon inserting a tubing segment.

FIG. 3 illustrates a schematic side view of the tube roller pump with opened cover 50 pivoted upwards about a hinge 51 for inserting a tubing segment 30. The cover 50 can also be a laterally pivoting cover 50, however. The rocker arm 23 is swiveled out about the pivoting axis 26 and is pivoted upwards, respectively, in the view shown in FIG. 3.

Figure 4:
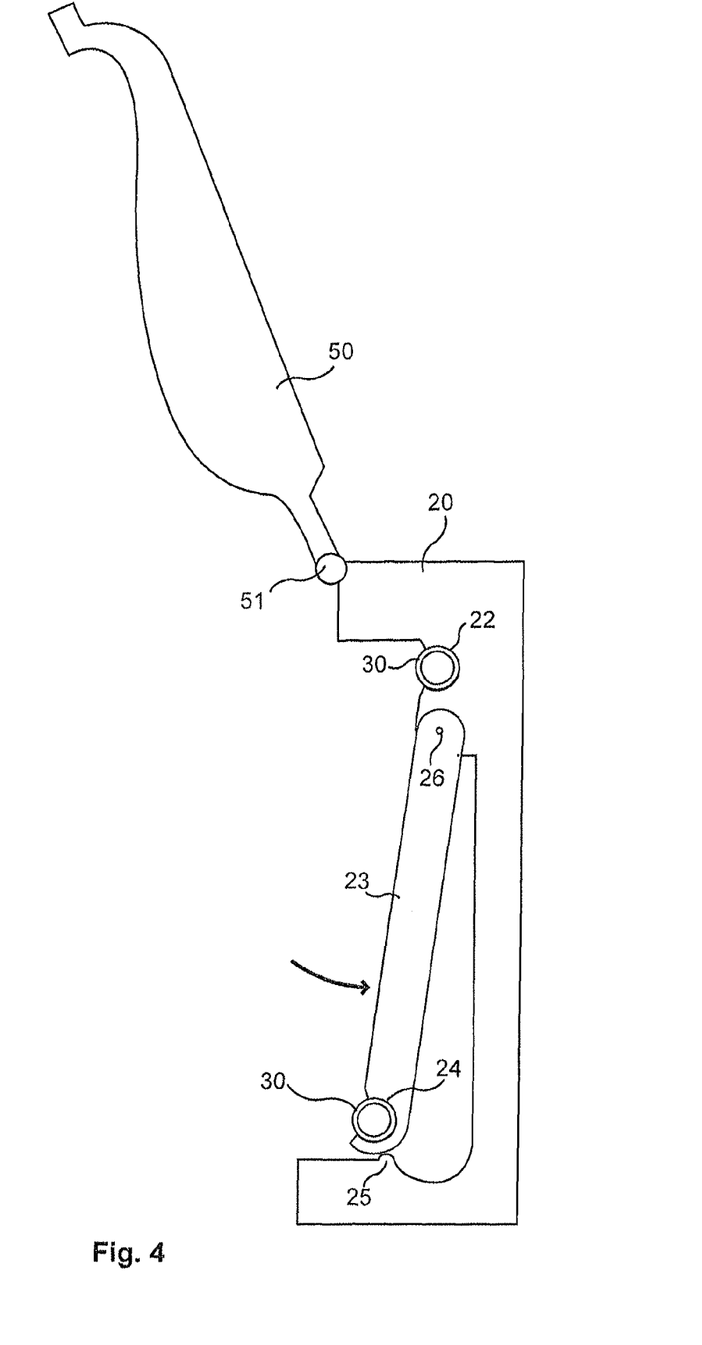
FIG. 4 a schematic side view of a tube roller pump according to FIG. 3 upon pressing the rocker arm into the stop mechanism.

The one end of the tubing segment 30 is pressed into the upper receiving portion 22, this motion being represented by an arrow in FIG. 3. This applies mutatis mutandis to the other end of the tubing segment 30 which is pressed into the lower receiving portion 24. Subsequently the rocker arm 23 together with the tubing segment 30 disposed thereon is pressed toward the bottom of the indentation in the pump housing 20 in order to bring the rocker arm 23 into the threading position (to the right in FIG. 4). For maintaining the rocker arm 23 in the threading position, in the lower area of the rocker arm 23 a stop mechanism is formed. For this purpose, e.g. a stop catch geometry 25 is provided over which the lower area of the rocker arm 23 has to be pressed before it engages in a receiving portion of the pump housing 20 located there behind.

Figure 5:
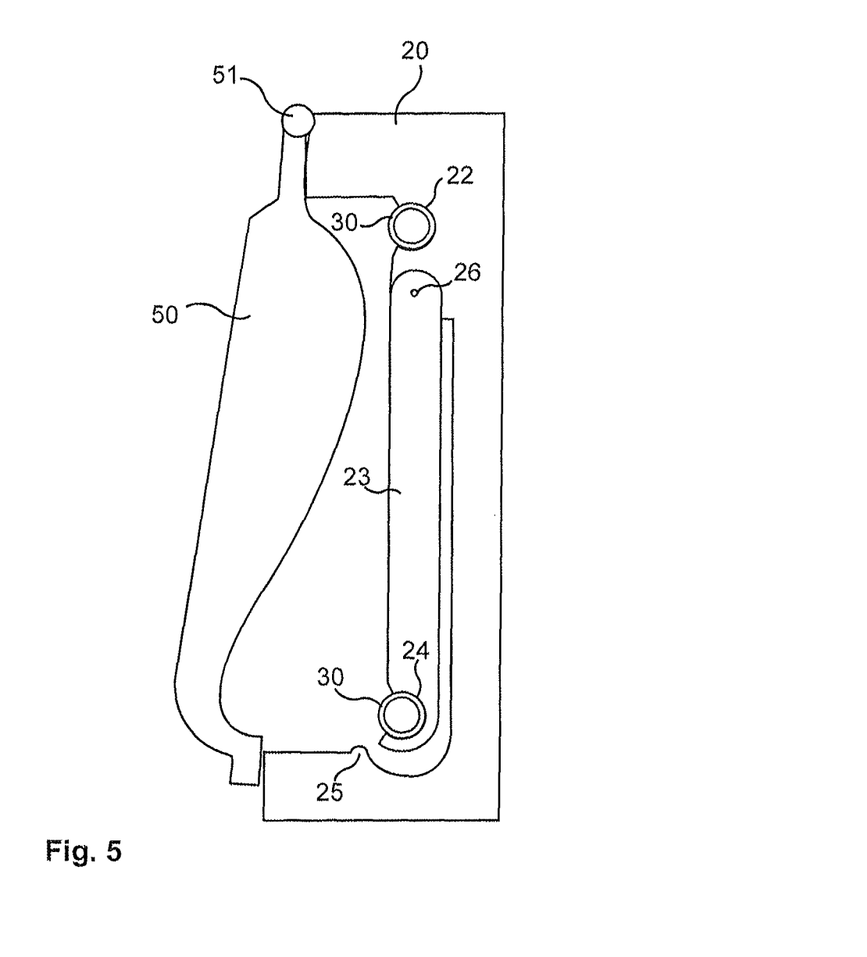
FIG. 5 a schematic side view of a tube roller pump according to FIG. 3 with a closed cover in the threading position.

Preferably detection means (not shown) are provided to detect the position of the rocker arm 23 in the engaged threading position. Said threading position at the same time constitutes the therapy position. After the rocker arm 23 has engaged in this position, the cover 50 is closed and the automated threading operation can be started. Preferably, also detecting means for detecting the state of the cover 50 are provided so that the threading operation can be started as soon as the detecting means ensure that the rocker arm 23 is in the threading position and the cover 50 is closed (FIG. 5).

Figure 6:
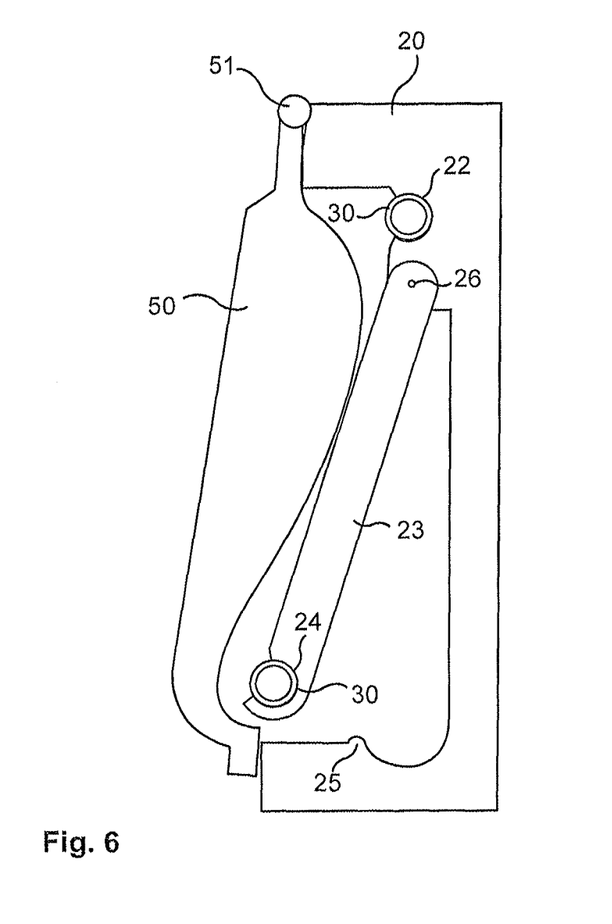
FIG. 6 a schematic side view of a tube roller pump according to FIG. 3 with a closed cover in the unthreading position.

During threading the rotor 40 is slowly rotated so that the guide pins 41 and 42 perform the threading operation. At least one guide pin 41 or 42, respectively, moves outwardly along the tubing segment 30 and presses the same between the rotor 40 and the bearing surface 21. In order to initiate the unthreading operation in the wake of the therapy, the rocker arm 23 is pulled to the left together with the tubing segment 30 by a user, as is shown in FIG. 6. The cover 50 serves as counter-bearing or stop against which the rocker arm 23 can be pulled up to the stop. Said stop defines the unthreading position which can equally be detected by detecting means. When the cover 50 is closed and the rocker arm 23 is provided in the unthreading position, the rotor 40 can slowly move the guide pins between the pump bottom and the tubing segment 30, thereby the tubing segment 30 being lifted out between the rotor 40 and the bearing surface 21.

Figure 7A:
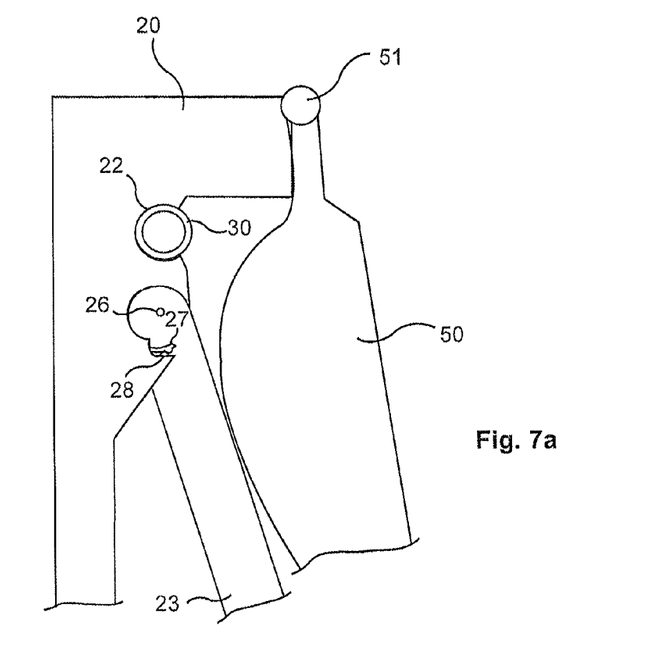
FIG. 7a an enlarged view of the stop mechanism in the area of the pivoting axis in the unthreading position.
Figure 7B:
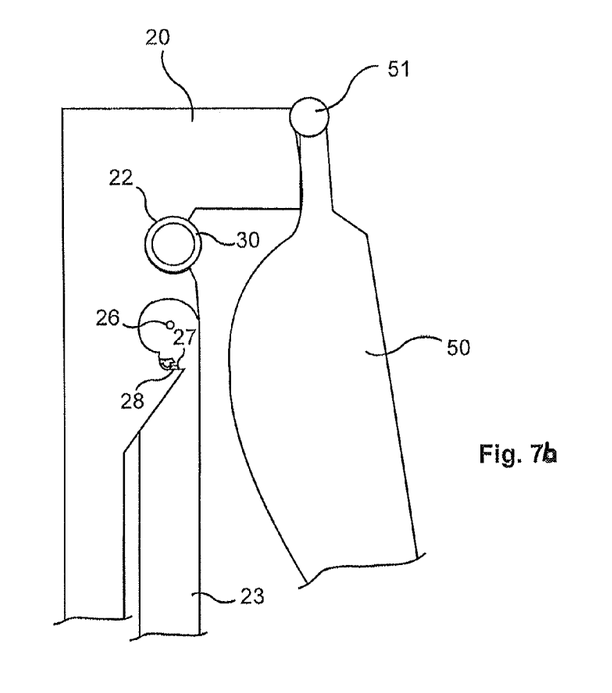
FIG. 7b an enlarged view of the stop mechanism in the area of the pivoting axis in the threading position.

For maintaining the rocker arm 23 in the unthreading position, for instance a spring mechanism is provided in the area of the pivoting axis 26. The functioning of said spring mechanism can be inferred from FIGS. 7a and 7b representing an enlarged cutout of the pivot. In FIG. 7a the rocker arm 23 is shown in the unthreading position, on this side of the rocker arm 23 an arc-shaped spring element 27 being arranged on the rocker arm 23. Said spring element 27 extends substantially around the pivoting axis 26 and includes a stop element in the form of an elevation. In this position of the rocker arm 23 said elevation abuts against the catch nose 28 formed at the pump housing 20. The rocker arm 23 is thus locked in the unthreading position at the pivoting axis 26 and does not slip or swivel back solely by the weight of the rocker arm 23.

When the rocker arm 23 swivels from the unthreading position into the threading position, it need not only be pressed into the lower locking (stop catch 25) but it has to overcome also the locking in the area of the pivoting axis 26. This is illustrated in FIG. 7b, wherein it is evident that the spring element 27 has been pulled over the catch nose 28 at the pump housing 20 upon pivoting about the pivot.

The invention claimed is:

1. A tube roller pump for a medical device for extracorporeal blood treatment comprising a pump housing having a bent bearing surface and a rotor rotatable inside the bearing surface, to receive a tubing segment between the bearing surface and the rotor in the form of a loop, wherein
   a fixed first receiving portion configured to accommodate a first end of the loop-shaped tubing segment such that the first end of the loop-shaped tubing segment is held in place within the fixed first receiving portion, the fixed first receiving portion provided at the pump housing, and
   a rocker arm provided at the pump housing and spaced from the fixed first receiving portion, wherein
   the rocker arm is configured to rotate about a pivoting axis,
   the rocker arm includes a second receiving portion configured to accommodate a second end of the loop-shaped tubing segment, such that the second end of the loop-shaped tubing segment is held in place within the second receiving portion, and such that the second receiving portion and the second end of the loop-shaped tubing segment are configured to rotate about the pivoting axis with the rocker arm, such that the second end of the loop-shaped tubing segment is configured to rotate into at least a first position and a second position about the pivoting axis while the first end of the loop-shaped tubing segment is held stationary within the fixed first receiving portion, and
   the first position constitutes a threading position and the second position constitutes an unthreading position for the tubing segment.

2. The tube roller pump according to claim 1, wherein the receiving portions are in the form of undercut recesses into which the respective end of the tubing segment are pressed when received.

3. The tube roller pump according to claim 1, wherein means for automated threading and unthreading of the tubing segment between the rotor and the bearing surface are provided at the rotor.

4. The tube roller pump according to claim 3, wherein at least one especially radially projecting guide pin is disposed at the periphery of the rotor.

5. The tube roller pump according to claim 4, wherein in the unthreading position the second receiving portion is at a position at which the at least one guide pin moves upon rotation of the rotor between the tubing segment and the bottom of the pump housing and thereby lifts the tubing segment out of the pump housing.

6. The tube roller pump according to claim 4, wherein in the threading position the second receiving portion is at a position at which the at least one guide pin moves upon rotation of the rotor above the tubing segment and thereby presses the tubing segment into the pump housing.

7. The tube roller pump according to claim 1, wherein means for maintaining the rocker arm in the threading position are provided.

8. The tube roller pump according to claim 7, wherein means for locking the rocker arm with the pump housing are provided spaced apart from the pivoting axis.

9. The tube roller pump according to claim 8, wherein at the pump housing a stop catch is formed which forms a stop mechanism together with the geometry of the rocker arm, the locking being effected in the area of the second receiving portion.

10. The tube roller pump according to claim 1, wherein means for maintaining the rocker arm in the unthreading position are provided.

11. The tube roller pump according to claim 10, wherein a stop catch forming a stop mechanism together with a stop spring at the rocker arm is formed at the pump housing.

12. The tube roller pump according to claim 11, wherein the stop spring is bent and arranged in the area of the pivoting axis at the rocker arm, the bending of the stop spring substantially extending around the pivoting axis.

13. The tube roller pump according to claim 1, wherein the geometry and/or the material of the rocker arm are configured so that the rocker arm is detectable at least in the threading position and/or the unthreading position directly by detecting means at the tube roller pump.

14. The tube roller pump according to claim 13, wherein at least a magnet and/or a ferromagnetic material is/are arranged at the rocker arm and the detecting means include at least a Hall sensor.

15. A medical device for extracorporeal blood treatment comprising the tube roller pump according to claim 1; wherein the tubing segment, when received, is configured to receive blood via a feed line and to discharge blood via a discharge line.

* * * * *